US009138571B2

(12) United States Patent
Shah et al.

(10) Patent No.: US 9,138,571 B2
(45) Date of Patent: Sep. 22, 2015

(54) HIGH-DENSITY PERCUTANEOUS CHRONIC CONNECTOR FOR NEURAL PROSTHETICS

(71) Applicants: Kedar G. Shah, San Francisco, CA (US); William J. Bennett, Livermore, CA (US); Satinderpall S. Pannu, Pleasanton, CA (US)

(72) Inventors: Kedar G. Shah, San Francisco, CA (US); William J. Bennett, Livermore, CA (US); Satinderpall S. Pannu, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 13/898,418

(22) Filed: May 20, 2013

(65) Prior Publication Data

US 2014/0273545 A1  Sep. 18, 2014

Related U.S. Application Data

(60) Provisional application No. 61/649,194, filed on May 18, 2012.

(51) Int. Cl.
 *H02G 3/18* (2006.01)
 *A61M 39/02* (2006.01)

(52) U.S. Cl.
 CPC ... *A61M 39/0247* (2013.01); *A61M 2039/0261* (2013.01); *A61M 2039/0267* (2013.01)

(58) Field of Classification Search
 CPC ............ A61M 39/0247; A61M 2039/0261; H02G 3/065; H02G 3/18; H02G 3/22
 USPC .................................... 174/659; 439/39
 See application file for complete search history.

(56) References Cited

U.S. PATENT DOCUMENTS

| | | | |
|---|---|---|---|
| 6,995,316 B1 * | 2/2006 | Goto | 174/659 |
| 8,552,293 B2 * | 10/2013 | Tolbert, Jr. | 174/50.5 |
| 8,957,327 B2 * | 2/2015 | Ahire et al. | 174/650 |
| 2009/0215283 A1 * | 8/2009 | Du | 439/39 |

* cited by examiner

*Primary Examiner* — Dhirubhai R Patel
(74) *Attorney, Agent, or Firm* — James S. Tak

(57) ABSTRACT

A high density percutaneous chronic connector, having first and second connector structures each having an array of magnets surrounding a mounting cavity. A first electrical feedthrough array is seated in the mounting cavity of the first connector structure and a second electrical feedthrough array is seated in the mounting cavity of the second connector structure, with a feedthrough interconnect matrix positioned between a top side of the first electrical feedthrough array and a bottom side of the second electrical feedthrough array to electrically connect the first electrical feedthrough array to the second electrical feedthrough array. The two arrays of magnets are arranged to attract in a first angular position which connects the first and second connector structures together and electrically connects the percutaneously connected device to the external electronics, and to repel in a second angular position to facilitate removal of the second connector structure from the first connector structure.

7 Claims, 4 Drawing Sheets

HIGH-DENSITY PERCUTANEOUS CHRONIC CONNECTOR FOR NEURAL PROSTHETICS

I. CLAIM OF PRIORITY IN PROVISIONAL APPLICATION

This patent document claims the benefit and priority of U.S. Provisional Application No. 61/649,194, filed on May 18, 2012, hereby incorporated by reference.

II. FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

III. FIELD OF THE INVENTION

The present invention relates to neural prosthetic devices and connectors, and more particularly to a high-density percutaneous chronic connector for neural prosthetics with a magnetic clamping and release mechanism.

IV. BACKGROUND OF THE INVENTION

Neural prosthetic devices that electrically stimulate and/or record signals from neural tissue make scientific interaction and exploration of the brain possible, with the goal of studying and ultimately treating a wide range of neural disorders and conditions, such as for example, depression, Parkinson's disease, epilepsy, and deafness. Such neural prosthetic devices typically employ microelectrode arrays with exposed electrodes that allow electrical signals to be received from and transmitted to the brain via a series of electrical paths connected to an external computer. In particular, such devices may consist of a percutaneous system which includes an implanted microelectrode array, external electronics, and a conduit or connector to carry electrical signals between the neural tissue and external electronics. The connector typically consists of two parts which connect to each other: (1) a percutaneous connector which is connected to the implanted array and therefore remains attached to the subject, and (2) an external connector which is connected by leads to the external electronics. These connectors may be temporarily electrically connected in order to transmit electrical signals during a study or treatment, and subsequently disconnected when not in use.

Over the past few decades, the focus of research on such neural prosthetic devices has been on the density of electrodes, electrode materials, and stimulation parameters that permit interaction with the brain. While in recent years, many such electrode and stimulation technologies have been optimized, research has often been limited to short-term studies due to the lack of bio-compatibility of device materials and connectors, and the inability to reliably transit or record signals from the tissue over a long time period.

Current connectors that carry electrical signals are limited because they use non-bio-compatible materials and electrical interconnects with limited lifetime. Additionally, they use macro-fabrication technologies that limit the density of electrical interconnects, thus making the size of connectors too large for practical long-term use.

V. SUMMARY OF THE INVENTION

One aspect of the present invention includes a high density percutaneous chronic connector, comprising: a first connector structure having an array of magnets surrounding a mounting cavity and means for attaching the first connector structure to a subject; a first electrical feedthrough array seated in the mounting cavity of the first connector structure and having a bottom side for connecting to a percutaneously connected device; a second connector structure having an array of magnets surrounding a mounting cavity; a second electrical feedthrough array seated in the mounting cavity of the second structure and having a top side for connecting to external electronics; and a feedthrough interconnect matrix positioned between a top side of the first electrical feedthrough array and a bottom side of the second electrical feedthrough array, and having a plurality of electrically conductive wires arranged in a dielectric substrate to electrically connect the first electrical feedthrough array to the second electrical feedthrough array; and wherein the two arrays of magnets are arranged to attract in a first angular position to connect the first and second connector structures together and electrically connect the percutaneously connected device to the external electronics, and to repel in a second angular position to facilitate removal of the second connector structure from the first connector structure.

The present invention is directed to a chronic, percutaneous electrical connector for neural prosthetics that is bio-compatible for chronic use without eliciting a cyto-toxic response from the patient or animal. The connector of the present invention includes a first connector structure having an array of magnets surrounding a mounting cavity and means for attaching the first connector structure to a subject, such as for example mounting flanges protruding from the sides of the structure for fastening a screw or other fastener. A first electrical feedthrough array is seated in the mounting cavity of the first connector structure and having a bottom side for connecting to a percutaneously connected device.

A second connector structure is provided having an array of magnets surrounding a mounting cavity, and a second electrical feedthrough array is seated in the mounting cavity of the second structure and having a top side for connecting to external electronics. And a feedthrough interconnect matrix is positioned between a top side of the first electrical feedthrough array and a bottom side of the second electrical feedthrough array, and having a plurality of electrically conductive wires arranged in a dielectric substrate to electrically connect the first electrical feedthrough array to the second electrical feedthrough array.

The two arrays of magnets are arranged to attract in a first angular position to connect the first and second connector structures together and electrically connect the percutaneously connected device to the external electronics, and to repel in a second angular position to facilitate removal of the second connector structure from the first connector structure. This magnetic connection/clamping mechanism provides for reducing connection and disconnection forces (low-force clamping) between the first connector structure (i.e. implanted connector) and the second connector structure (i.e. external connector). This magnetic connector arrangement also includes a safety disengagement feature which disengages the connector safely without damaging the device or injuring the test subject. In particular, by arranging magnets of alternating polarities, a simple twist of the second connector structure on the first connector structure enables a repelling force between magnets of the same polarity to facilitate disconnection and removal. Such magnetic connection of the present invention enables high reliability of electrical connections to survive thousands of connect/disconnect cycles. In an example embodiment the connector structures may be keyed for automatic alignment to allow ease-of-use, such as for example in experiments on awake animals. In particular, the first connector structure and the second connector structure may be keyed to connect at a known angular position which aligns the feedthroughs of the first electrical feedthrough array with the second electrical feedthrough array. Furthermore, the first connector structure and the second connector structure may be particularly keyed by arranging the arrays of magnets of the first and second connector structures so that all magnet combinations attract only at the known angular position.

In a particular example embodiment, the second connector structure is separated into three components, including an annular magnet-carrying portion with the array of magnets mounted thereon, an annular cover portion connected to the annular magnet-carrying portion, and a feedthrough array-carrying portion surrounding the mounting cavity and rotatably positioned to free-spin between the annular magnet-carrying portion and the annular cover portion. Furthermore, the first connector structure and the feedthrough array-carrying portion of the second connector structure may be keyed to connect at a known angular position which aligns the feedthroughs of the first electrical feedthrough array with the second electrical feedthrough array.

The present invention may be used, for example, for long-term electrical stimulation of, or recording from cortical or peripheral neural tissue; cochlear implants; visual prosthetics; treatments for neural disorders such as Parkinson's disease, epilepsy, deep-brain stimulation for depression, diseases affecting motor control, micturition, paralysis, etc.

VI. BRIEF DESCRIPTION OF THE DRAWINGS

The accompanying drawings, which are incorporated into and form a part of the disclosure, are as follows.

VII. DETAILED DESCRIPTION

Figure 1:
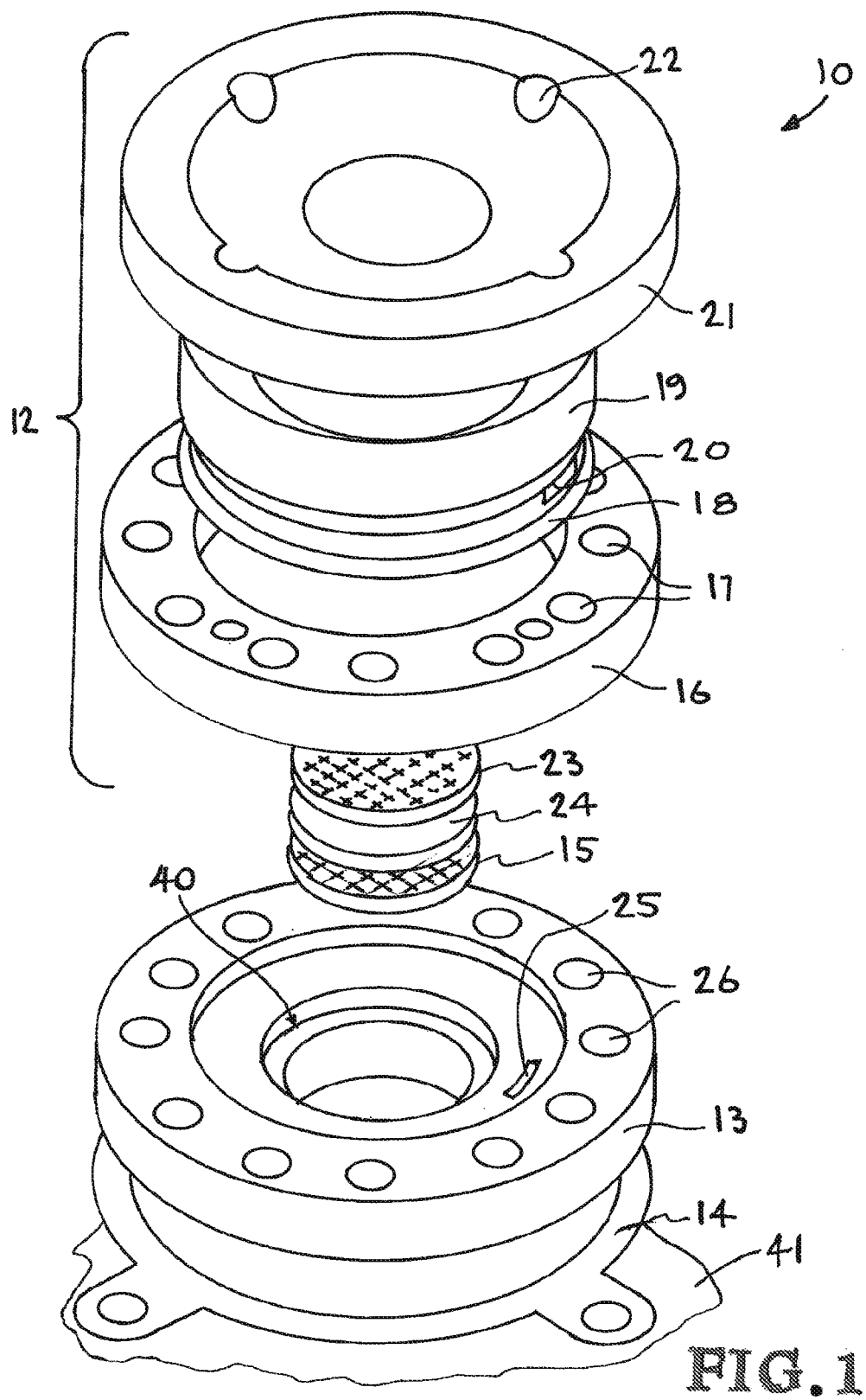
FIG. 1 is an exploded perspective view of an example embodiment of the chronic connector of the present invention.
Figure 2:
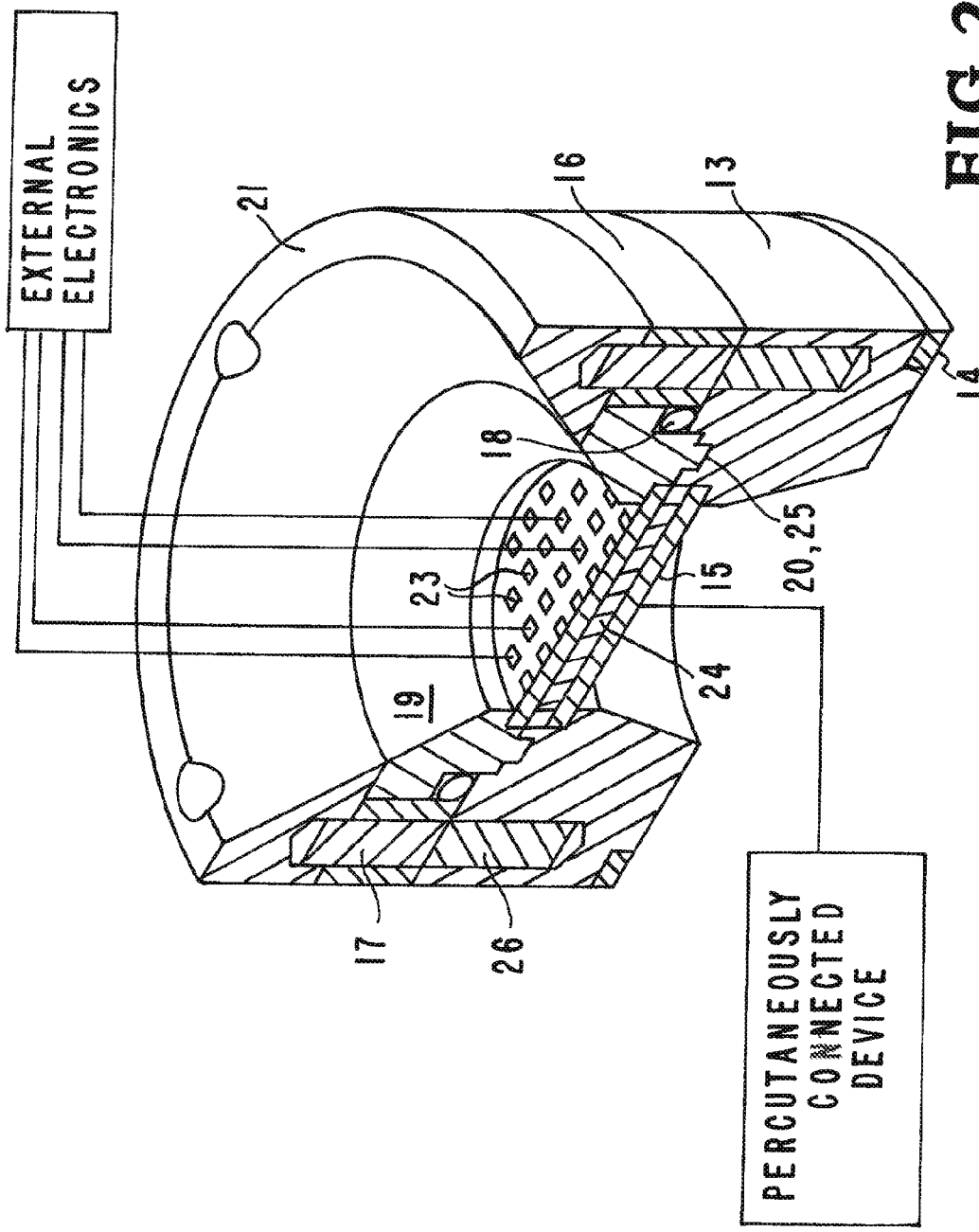
FIG. 2 is a perspective view of the chronic connector of FIG. 1 shown assembled and partially cut away.

Turning now to the drawings, FIGS. 1 and 2 show a first example embodiment of the chronic connector of the present invention, generally indicated at 10. FIG. 1 in particular shows the embodiment in exploded view, while FIG. 2 shows the embodiment assembled and connected. The chronic connector generally consists of five main parts, including a first connector structure 13 having a substantially annular configuration surrounding a mounting cavity 40, with an array of magnets 26 also perimetrically positioned around the mounting cavity on a top side of the structure 13. A key flange 20 is also shown for mating with a key slot 25. The first connector structure may be attached to the patient or animal (e.g. shown at reference character 41) by, for example a separate screw plate 14 having mounting flanges through which fasteners may be used. Or in the alternative mounting flanges may be provided on the first connector structure 13 itself. Attachment can be done with screws (through the screw plate) and/or acrylic or bio-compatible cement that mechanically anchors the connector to the test subject. The top portion of the first connector contains the magnets for the clamping mechanism, which will be described below.

The second main part includes a first electrical feedthrough array 15, which is also shown seated in the mounting cavity of the first connector structure 13 and having a bottom side for connecting to a percutaneously connected neural interface device (not shown). Connection may be made to the electrical feedthrough array 15 using an electrical interconnect method such as rivet bonding, conductive epoxy attachment, or flip-chip bonding. It is appreciated that the bottom side of the feedthrough array electrically connects to the top side of the array, which is shown adjacent a feedthrough interconnect matrix 24.

The third main part includes the feedthrough interconnect matrix 24 which is positioned between a top side of the first electrical feedthrough array 15 and a bottom side of the second electrical feedthrough array 23, and has a plurality of electrically conductive wires arranged in a dielectric substrate to electrically connect the first electrical feedthrough array to the second electrical feedthrough array. The interconnect matrix 24 contains, for example, a matrix of wires embedded into a silicone substrate, and allows repeatable connection/disconnection between the external connector and the percutaneous connector. In a particular embodiment, the wires protrude above and below the silicone. The density of wires is greater (>2×) than the density of contacts on the electrical feedthrough. This allows electrical interconnection without having to do high accuracy alignment of the interconnector. The interconnect matrix may contain wires angled (pictured below), or orthogonal to the silicone substrate.

The fourth main part includes a second connector structure 12 also shown comprising three main components, a first external clamp portion 16 having an array of magnets 17, an external connector 19 surrounding a mounting cavity in which the array 23 is rotatably seated, and a second external clamp portion 21 connected to the first external clamp portion 16, such as by fasteners mounted through holes, e.g. 22. An O-ring 18 (e.g. silicone or bio-compatible polymer) is also shown provided to act as a moisture and contamination barrier to prevent shorting of contacts.

And the fifth main part is a second electrical feedthrough array 23 that is seated in the mounting cavity of the second structure and having a top side for connecting to external electronics. This array 23 is preferably rotatably seated in the mounting cavity and capable of free-spinning therein. The top side of the array 23 is connectable to leads connecting to external electronics (not shown). An external cable may be electrically attached to the feedthrough array 23 and takes individual signals from the neural probe to the external electronics. This may consist of a flexible electrical cable connected to a printed circuit board, patterned silicon board, or electrical connector.

The chronic connector of the present invention preferably uses a magnetic clamping mechanism to engage/disengage the first and second connector structures. When engaged, the magnets line up with opposing polarities so that the external connector is clamped to the percutaneous connector by the external clamp. The magnets provide sufficient force for making electrical contact during device use. In particular, the two arrays of magnets are arranged to attract in a first angular position to connect the first and second connector structures together and electrically connect the percutaneously connected device to the external electronics, and to repel in a second angular position to facilitate removal of the second connector structure from the first connector structure.

Figure 3:
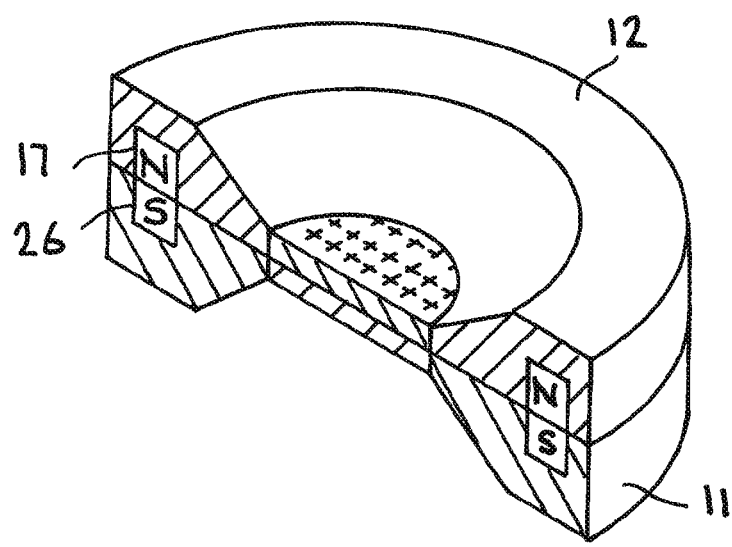
FIGS. 3 and 4 are perspective views of the chronic connector illustrating operation of the magnetic clamps for engaging and disengaging the external connector from the implanted connector.
Figure 4:
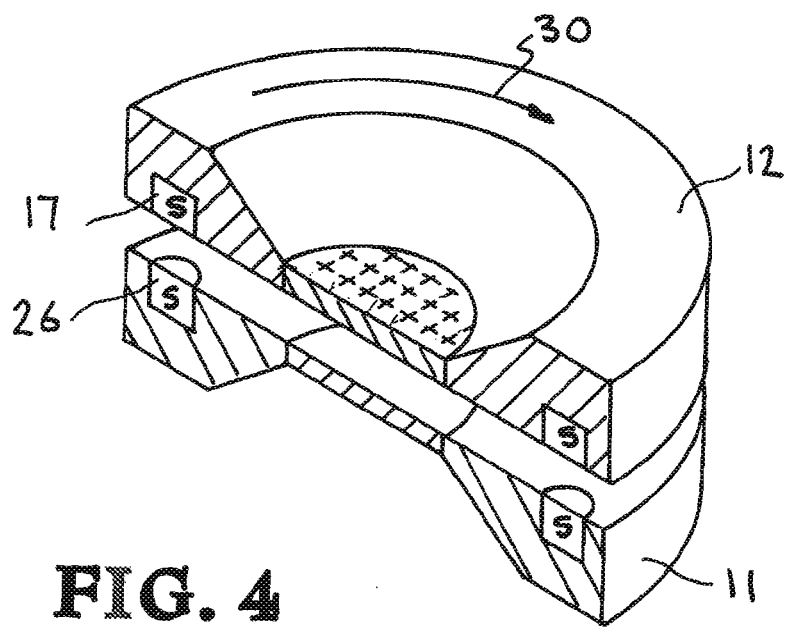
Figure 5:
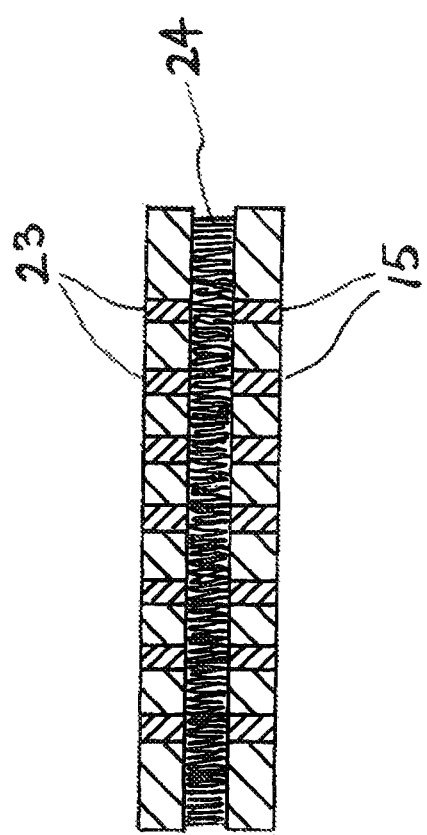
FIG. 5 shows a schematic side view of the feedthrough interconnectmatrix between the first electrical feedthrough array and the second electrical feedthrough array, with the feedthrough interconnect matrix shown having a plurality of electrically conductive wires arranged to electrically connect the first electrical feedthrough array to the second electrical feedthrough array.

A major requirement of such connectors is to have a low force of connection and disconnection so as to not damage the device or injure the test subject. To aid this, the magnets may be aligned in a circular array with magnets of opposing polarities lined up. This allows the user to engage/disengage the connector by rotating the external clamp. Since a small rotation will line up magnets with equal polarities, they will provide a repelling force, which aids in the release of the clamp without requiring additional force from the user. FIGS. 3 and 4 show an example of magnet polarities for such a clamp. The arrangement of magnets is not restricted to a circular array in order to achieve this style of clamping. The magnets may be rare-earth magnets, with the option of coating with a bio-compatible material (polymer, metal, ceramic).

When the neural interface is not actively in use, it is desirable to have the test subject be able to freely move, without being tethered to the electronics. The chronic connector of the present invention uses a protective cap with an O-ring and magnetic clamp that seals the electrical interconnects during non use. This cap may be made of biocompatible metal.

Fabrication and assembly of the chronic connector components of the present invention may include, for example, as follows. The electrical feedthrough arrays may be fabricated from alumina or other insulating ceramic with platinum or other bio-compatible vias. Metal patterned with a bio-compatible metal stack containing any combination of titanium, platinum, ruthenium, and gold. Feedthrough arrays may be attached to the connector either with non-conductive epoxy, metal braze, or welding process. The screw plate may be fabricated from bio-compatible metal such as Titanium, niobium, surgical grade stainless steel, gold, platinum, and alloys of each. The first and second connector structures may be made of the same bio-compatible material, similar to the screw plate. The temporary interconnect matrix may be made, for example, from silicone with bio-compatible embedded metal wires, or coated metal wires.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. A high density percutaneous chronic connector, comprising:
    a first connector structure having an array of magnets surrounding a mounting cavity and means for attaching the first connector structure to a subject;
    a first electrical feedthrough array seated in the mounting cavity of the first connector structure and having a bottom side for connecting to a percutaneously connected device;
    a second connector structure having an array of magnets surrounding a mounting cavity;
    a second electrical feedthrough array seated in the mounting cavity of the second structure and having a top side for connecting to external electronics; and
    a feedthrough interconnect matrix positioned between a top side of the first electrical feedthrough array and a bottom side of the second electrical feedthrough array, and having a plurality of electrically conductive wires arranged in a dielectric substrate to electrically connect the first electrical feedthrough array to the second electrical feedthrough array; and
    wherein the two arrays of magnets are arranged to attract in a first angular position to connect the first and second connector structures together and electrically connect the percutaneously connected device to the external electronics, and to repel in a second angular position to facilitate removal of the second connector structure from the first connector structure.

2. The high density percutaneous chronic connector of claim 1,
    wherein the first connector structure and the second connector structure are keyed to connect at a known angular position which aligns the feedthroughs of the first electrical feedthrough array with the second electrical feedthrough array.

3. The high density percutaneous chronic connector of claim 2,
    wherein the first connector structure and the second connector structure are keyed by arranging the arrays of magnets of the first and second connector structures so that all magnet combinations attract only at the known angular position.

4. The high density percutaneous chronic connector of claim 1,
    wherein the means for attaching the first connector structure to the subject includes mounting flanges for fastening the first connector structure with fasteners.

5. The high density percutaneous chronic connector of claim 1,
    wherein the second connector structure includes an annular magnet-carrying portion with the array of magnets mounted thereon, an annular cover portion connected to the annular magnet-carrying portion, and a feedthrough array-carrying portion surrounding the mounting cavity and rotatably positioned to free-spin between the annular magnet-carrying portion and the annular cover portion.

6. The high density percutaneous chronic connector of claim 5,
    wherein the first connector structure and the feedthrough array-carrying portion of the second connector structure are keyed to connect at a known angular position which aligns the feedthroughs of the first electrical feedthrough array with the second electrical feedthrough array.

7. The high density percutaneous chronic connector of claim 1,
    wherein the arrays of magnets of the first and second connector structures are arranged in alternating polarity.

* * * * *